(12) United States Patent
Axelsen et al.

(10) Patent No.: US 6,316,427 B1
(45) Date of Patent: Nov. 13, 2001

(54) TREATMENT FOR DIABETES

(76) Inventors: Mette Axelsen, Persvägen 11A, SE-433 64, Sävedalen; Ulf Smith, Strandrågsvägen 8, SE-434 94 Vallda, both of (SE)

( * ) Notice: Subject to any disclaimer, the term of this patent is extended or adjusted under 35 U.S.C. 154(b) by 0 days.

(21) Appl. No.: 09/543,096

(22) Filed: Apr. 4, 2000

(51) Int. Cl.[7] .................................................. A61K 31/715
(52) U.S. Cl. .................................................................. 514/60
(58) Field of Search .................................................. 514/60

(56) References Cited

U.S. PATENT DOCUMENTS

| | | |
|---|---|---|
| 5,605,893 | 2/1997 | Kaufman . |
| 5,776,887 * | 7/1998 | Wilbert et al. ............................ 514/2 |
| 5,843,921 | 12/1998 | Kaufman . |
| 5,866,555 * | 2/1999 | Bell et al. ............................... 514/60 |

OTHER PUBLICATIONS

"Nocturnal and Postprandial Metabolism in Diabetes Mellitus", Mette Axelsen, Published: Apr. 8, 1999.

A randomized blinded trial of uncooked cornstarch to diminish nocturnal hypoglycemia at Diabetes Camp, Francine R. Kaufman et al., *Diabetes Research and Clinical Practice*, vol. 30, pp. 205 to 209 (1955).

"Use of Uncooked Cornstarch to Avert Nocturnal Hypoglycemia in Children and Adolescents With Type 1 Diabetes", Francine R. Kaufman et al., *Journal of Diabetes and Its Complications*, vol. 10, pp. 84 to 87 (1996).

"Evaluation of a snack bar containing uncooked cornstarch in subjects with diabetes." Francine R. Kaufman *Diabetes Research and Clinical Practice*, vol. 35, pp. 27 to 33 (1997).

* cited by examiner

Primary Examiner—James H. Reamer

(57) ABSTRACT

A method for improving tolerance in a human suffering from impaired glucose tolerance including both IGT and Diabetes Mellitus Type 2, comprising ingesting a therapeutic amount of slow-release starch at bedtime.

Figure 1:
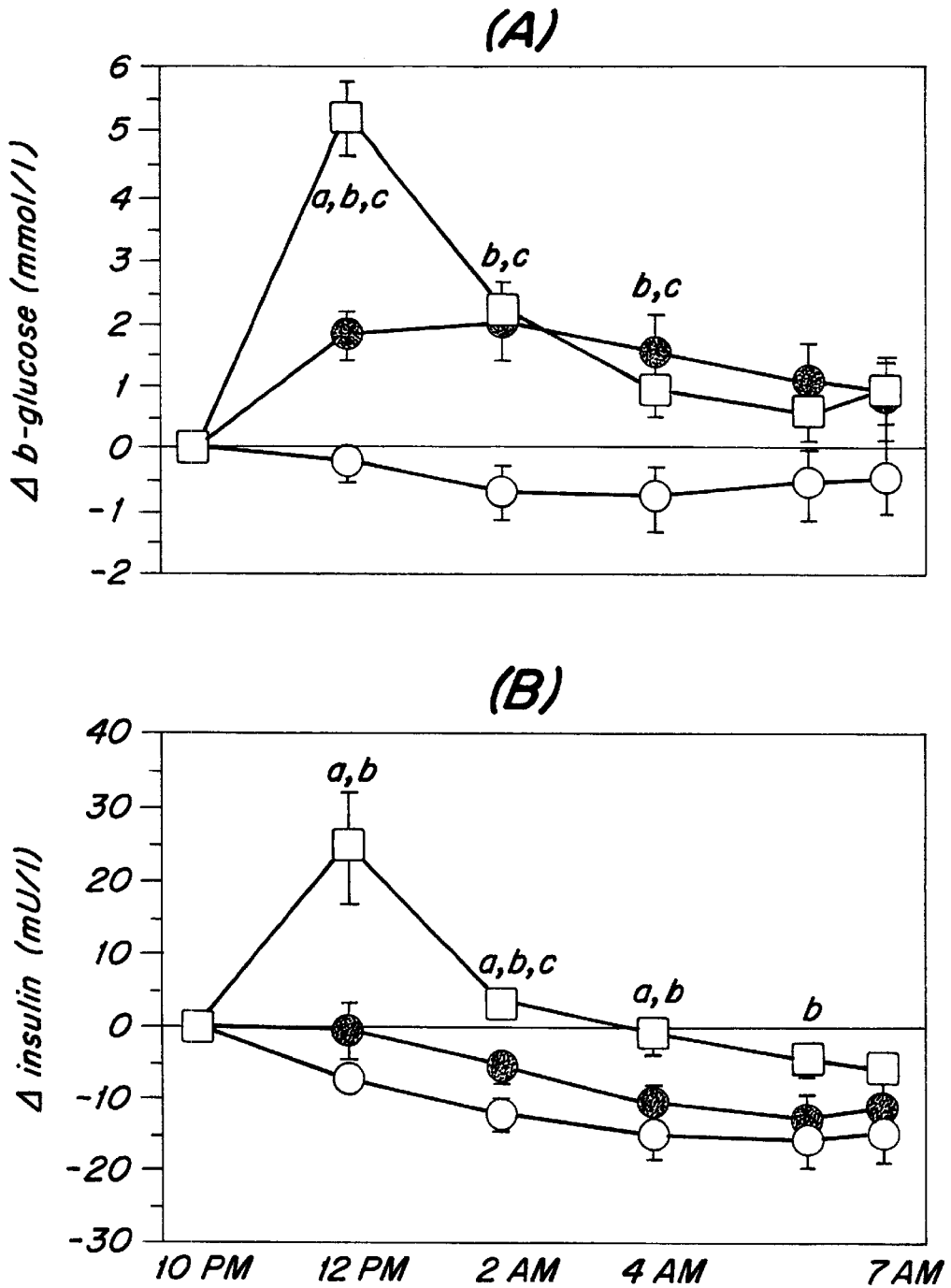

The preferred type of starch for use in this method is natural cornstarch.

20 Claims, 2 Drawing Sheets

Overnight responses in blood glucose (A) and plasma insulin (B) following bedtime ingestion of uncooked cornstarch (-●-), whole meal bread (-□-) or placebo (-○-) at bedtime in NIDDM patients, [a]$p<0.05$ whole meal bread vs. uncooked cornstarch; [b]$p<0.05$ whole meal bread vs. placebo; [c]$p<0.05$ uncooked cornstarch vs. placebo.

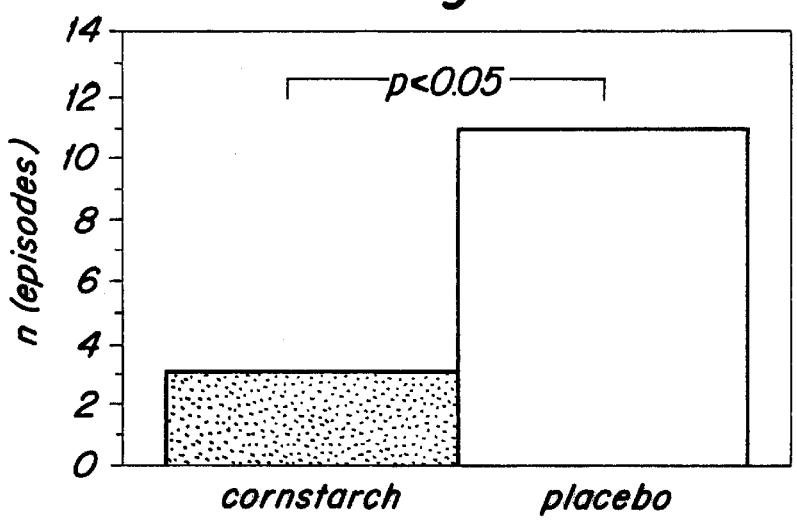

Total number of selfestimated hypoglycemic episodes (BG recordings <3.0mM) at 3 AM, out of 166 patient nights, following ingestion of uncooked cornstarch (▧) or placebo (□) supplement at bedtime.

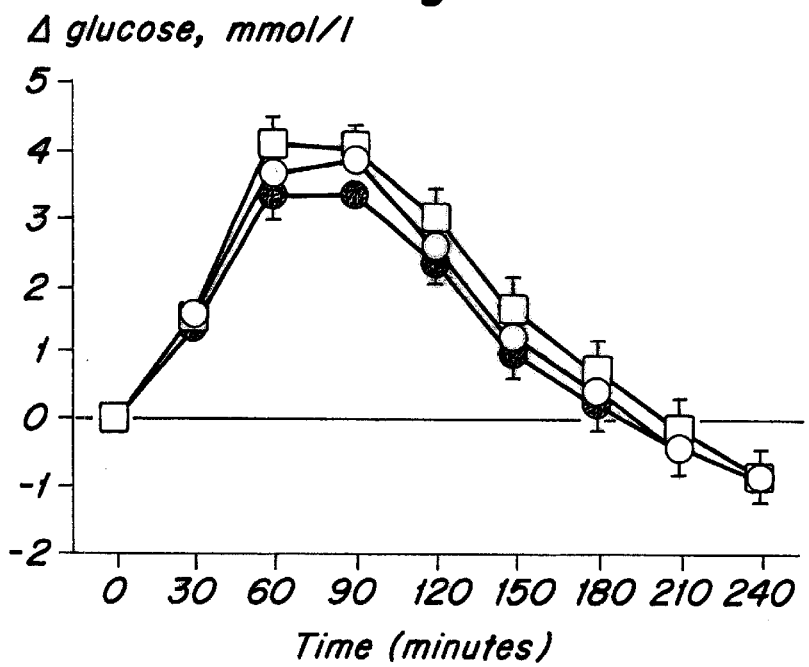

Mean glucose levels during a standarized breakfast in 16 Type 2 diabetic patients after ingestion at 22.00 h the previous evening of uncooked cornstarch (●), white bread (○) or carbohydrate-free placebo (□). Data represent means ±SE.

TREATMENT FOR DIABETES

The present invention relates to a method of improving glucose tolerance in a human suffering from impaired glucose tolerance (IGT), a prediabetic state, and manifest diabetes Mellitus Type 2.

BACKGROUND OF THE INVENTION

Both IGT and Type 2 diabetes are characterized by insulin resistance. They are parts of a major risk factor complex called the Insulin Resistance Syndrome (IRS). Individuals suffering from IGT or Type 2 diabetes exhibit important changes in diurnal insulin sensitivity, with an enhanced insulin resistance, and in Type 2 diabetes an increased endogenous glucose production at dawn, 4–9 AM. The first meal of the day, usually breakfast, produces a rapid switch from glucose production to glucose utilization. This event takes place under relative hypoinsulinemic conditions in diabetic patients. Both subjects with IGT and Type 2 diabetic patients have decreased carbohydrate tolerance at breakfast. This is also the case with Type 1 diabetic patients, but their postprandial hyperglycemia may be alleviated by an increased dose of exogenous insulin, However, in Type 2 diabetes, where the blood glucose is usually not well controlled by either endogenous or exogenous insulin, a sustained glucose production leads to an accentuated hyperglycemia at breakfast. The elevated nocturnal levels of free fatty acids (FFA) in Type 2 diabetic patients are probably involved in causing the fasting and postprandial hyperglycemia, since breakfast glucose tolerance is improved by FFA suppression using an antilipolytic agent, such as acipimox, Quite generally, it is known in the art to treat diabetic patients to diminish fluctuations in blood sugar levels and prevent hypoglycemic episodes using slowly absorbed or digested complex carbohydrates, such as natural cornstarch, Thus, U.S. Pat. Nos. 5,605,893 and 5,843,921 to Francine Kaufman are examples of prior art where therapeutic food compositions containing uncooked cornstarch are used in methods of treating diabetic patients. However, the state of the art does not even remotely suggest the use of slow release carbohydrates for improving glucose tolerance in humans suffering from such impaired glucose tolerance prior to or as part of disease in diabetes Mellitus Type 2.

SUMMARY OF THE INVENTION

The main object of the present invention is to provide a method for improving glucose tolerance in a human suffering roam diabetes Mellitus Type 2 or impaired glucose tolerance as a pre-stage of diabetes or obesity.

The method is preferably directed to improving postprandial glucose tolerance.

Yet another object of the invention is to provide such method comprising ingesting a therapeutic amount of slow-release starch, preferably cornstarch, at bedtime.

The invention is based on the surprising discovery that the glucose tolerance in humans suffering from such impaired tolerance can be significantly improved by the ingestion of a therapeutic amount of slow-release starch at bedtime. A preferred starch for such use is natural cornstarch, preferably contained in a palatable carrier.

Such carrier can be constituted by a liquid or a gel or it can be constituted by a carbohydrate other than starch. The carrier can be supplemented with a non-glucose sweetener, such as fructose, sorbitol, maltitol or an artificial sweetener.

Among artificial sweeteners useful in the invention there may be mentioned saccharine, aspartame and acesulfame.

The method according to the invention involves amounts of ingested slow-release carbohydrate varying from about 0.1 to about 1 g per kg bodyweight, especially about 0.2 to about 0.7 g per kg bodyweight.

DESCRIPTION OF SPECIFIC EMBODIMENTS ILLUSTRATING THE INVENTION

The present invention will be further illustrated below by specific examples which, however, must not be construed to restrict the invention other than according to the definition thereof in the appended claims. The specific examples are given in relation to the figures of the appended drawing wherein:

FIGS. 1A and B show the variation of the blood glucose concentration and plasma insulin levels between bedtime and the following morning following ingestion of conventional snacks and uncooked cornstarch;

FIG. 2 shows number of self-estimated hypoglycemic episodes comparing ingestion of uncooked cornstarch and placebo supplement ingested at bedtime; and FIG. 3 shows variation of mean glucose levels during a breakfast meal after ingestion the previous evening of cornstarch, white bread and a carbohydrate-free placebo.

In the following examples 60 Type 2 diabetic patients, 5 IGT and 12 Type 2, were studied, none of whom had clinically relevant diabetic neuropathy, nephropathy or retinopathy. The patients had adhered to an unchanged diabetes therapy for at least 3 months. 13 healthy relatives of Type 2 diabetic patients and 13 control subjects without known such heredity were also investigated. None of the subjects in Examples I–IV were treated with lipid-lowering agents. The characteristics of the subjects are shown in Table 1.

TABLE 1

| | Group | n | Male/Female | Age (years) | BMI (kg/m$^2$) | Laboratory baseline data | |
|---|---|---|---|---|---|---|---|
| Example I | Type 1 DM | 12 | 7/5 | 40 ± 9 | 22.9 ± 1.3 | FBG | 8.5 ± 0.5 mM, |
| | | | | | | HbA$_{1c}$ | 6.2 ± 0.7% |
| Examples I & II | Type 2 DM | 10 | 9/1 | 55 ± 9 | 29.0 ± 3.6 | FBG | 8.2 ± 1.6 mM, |
| | | | | | | HbA$_{1c}$ | 7.0 ± 0.9% |
| Examples 1 & III 'high dose' | Type 2 DM | 14 | 11/3 | 56 ± 7 | 29.2 ± 2.8 | FBG | 8.4 ± 1.7 mM, |
| | | | | | | HbA$_{1c}$ | 6.8 ± 1.0% |
| Example III | Type 2 DM | 12 | 7/5 | 61 ± 9 | 28.8 ± 2.7 | FBG | 7.6 ± 1.6 mM, |
| 'low dose' | IGT | 5 | 2/3 | | | HbA$_{1c}$ | 6.1 ± 0.9% |

TABLE 1-continued

| Group | n | Male/Female | Age (years) | BMI (kg/m$^2$) | Laboratory baseline data | |
|---|---|---|---|---|---|---|
| Example III 'low dose' | Type 2 DM | 12 | 7/5 | 60 ± 13 | 28.8 ± 5.3 | FBG<br>HbA$_{1c}$ | 7.2 ± 1.3 mM,<br>6.2 ± 0.9% |
| Example IV | Type 2 DM | 16 | 14/2 | 61 ± 9 | 29.2 ± 5.0 | FBG<br>HbA$_{1c}$ | 8.4 ± 1.7 mM,<br>6.5 ± 0.9% |

In the examples the digestibility rates of different foods were measured by a controlled in vitro enzymatic hydrolysis (Englyst H, Kingman S & Cummings J (1992): Classification and measurement of nutritionally important starch fractions. Eur.J.Clin.Nutr. 46 (suppl 2), 33–50). According to Englyst et al, their method gives reproducible estimates of starch digested in the small intestine (Englyst et al. 1992). The starch is classified as rapidly digestible starch and slowly digestible starch. Resistant starch, i.e. starch which passes into the colon, is calculated. The content of rapidly digestible starch in food correlates with corresponding values obtained by the glycemic index (GI) method (r=0.73, p<0.05)(Englyst H, Veenstra J & Hudson G (1996): Measurement of rapidly available (RAG) in plant foods: a potential in vitro predictor of the glycaemic response. Br.J.Nutr. 75, 327–37).

Conventional statistical methods were used, parametric or non-parametric as appropriate after having tested each effect variable for normality by means of a Normal plot (Altman D. Practical statistics for medical re-search. London; Chapman & Hall, 1994). Data which were serially collected over time were transformed to a summary measure of that individual, such as the AUC or the IAUC. Results are presented as means±standard errors of the mean (SE), if not otherwise stated. A two-tailed P-level of 5% or less is considered to be statistically significant.

EXAMPLE I

The aim of this study was to compare the nocturnal release profiles of uncooked cornstarch and a conventional bedtime snack in diabetic subjects. Two comparable groups of patients with Type 2 diabetes (10 and 14 patients, respectively) were admitted to the laboratory for overnight investigations of the blood glucose and insulin levels following the ingestion of the bedtime snacks at 22.00 h. One group (n=10) ingested a conventional snack consisting of whole-meal sandwiches (0.6 g of carbohydrates/kg body weight). The other group (n=14) consumed a similar amount of carbohydrates from uncooked cornstarch and, on another occasion, a starch-free placebo.

The two bedtime meals significantly raised the blood glucose level from 24.00–04.00 h in the Type 2 diabetic patients, when compared to type starch-free placebo. However, the conventional snack elicited a markedly different glucose profile (FIG. 1) and caused significant hyperglycemia at 24.00. Bedtime uncooked cornstarch ingestion led to a lower (2.9±0.5 vs. 5.2±0.6 mmol/l, p=0.01) and delayed (4.3±0.6 vs. 2.0±0.0 hours, p<0.01) blood glucose peak compared to the conventional snack.

EXAMPLE II

Type 1 diabetic patients were recruited from the Diabetes out-patient clinic at Sahlgrenska University Hospital. The patients were selected on the basis of having one or several episodes of severe hypoglycemia during the last year and/or at least one episode of nocturnal hypoglycemia each month and a history of hypoglycemia un-awareness. These problems are often seen in Type 1 diabetic subjects with a tight glycemic control and multiple injections of insulin. The body weight of the patients was normal (means±SD 72.7±10.9 kg, range 55.5–91.0 kg) and corresponded to a body mass index (BMI) below 25 kg/m$^2$. The patients were well-controlled, with HbA$_{1c}$ less or equal to 7.5% (ref. 3.3–5.3%). They were on an intensive treatment regimen, i.e. at least 3 daily doses of short-acting insulin prior to meals and one dose of intermediate acting (NPH) insulin at bedtime.

Type 1 diabetic patients were given 0.30 g uncooked cornstarch per kg of body weight. This amount had proven feasible in pilot studies.

The aim of this study was to examine the effect of uncooked cornstarch (0.30 g/kg body weight) in conjunction with the bedtime dose of NPH insulin on nocturnal hypoglycemia in Type 1 diabetic patients. Nocturnal hypoglycemia was assessed as the frequency of self-estimated hypoglycemia (blood glucose level <3.0 mmol/l) at 03.00 h.

The results were compared to those of a starch-free placebo in a double-blind, randomised crossover study with a seven-week washout period. Each period lasted for four weeks and nocturnal blood glucose levels were measured for two weeks.

Bedtime ingestion of uncooked cornstarch was associated with higher self-estimated blood glucose levels at 03.00 h (by ~2 mmol/l, p<0.01), as well as before breakfast (by ~1 mmol/l, p<0.05) when compared to placebo. Moreover, the four weeks of bedtime cornstarch ingestion was associated with a 70% reduction in the frequency of self-estimated hypoglycemic events at 03.00 h (p<0.05). There were no unfavourable changes in the levels of HbA$_{1c}$, total cholesterol, HDL-cholesterol or triglycerides by the bedtime supplement.

Effect of bedtime ingestion of 0.55 g uncooked cornstarch per kg body weight as compared to a placebo intake is illustrated in FIG. 2 as number of self-estimated hypoglycemic episodes. In this investigation the number of nocturnal biochemical hypoglycemic episodes, defined as a blood glucose level <3.0 mmol/l with or without symptoms at 3 AM, are given in FIG. 2. Out of 166 recordings at 3 AM, there were in total 11 hypoglycemic episodes in the placebo period. Following an identical number of recordings by each subject in the cornstarch period, this was reduced to 3 episodes (p<0.05).

EXAMPLE III

Type 2 diabetic patients were recruited by means of advertisement in a local newspaper. None of the patients were on insulin treatment, Their mean body weight was similar to that of the patients in Example II.

In 14 patients the effects of a 'high' dose of uncooked cornstarch (0.55 g/kg body weight) were studied. The inclusion criteria were a fasting blood glucose <12.0 mmol/l and $HbA_{1c}$<10.0%. Seven patients were treated with sulfonylurea (glipizide or glibenclamide), four with metformin and three with diet alone. One of the patients was lean (BMI <25kg/m$^2$) but BMI in all others was >27 kg/m$^2$. All patients had a waist-hip ratio >0.90.

The effects of a 'low' body dose of uncooked cornstarch (0.30 g/kg body weight) were studied in 24 Type 2 diabetic patients. The inclusion criteria were a fasting blood glucose <10.0 mmol/l and $HbA_{1c}$<8.0%. Moreover, patients treated with sulphonylurea were excluded. The patients were divided into two pair-wise matched groups, one group receiving cornstarch and the other a starch-free placebo. Two patients in the cornstarch group and four patients in the placebo group were treated with metformin. In both groups, five patients had a BMI of 25–27 kg/m$^2$ and seven patients a BMI >27 kg/m$^2$. Waist-hip ratio in the women was >0.85 and in the men >0.90.

After obtaining the data in Example 2 lower doses were tried. According to the data, 0.55 g of uncooked cornstarch/kg body weight was found to be sufficient to elicit an overnight second-meal effect in Type 2 diabetic patients. However, since that dose still represented a higher carbohydrate dose than that normally consumed as a bedtime snack, a lower dose, 0.30 g/kg body weight, was also investigated. The two doses are referred to as 'high' and 'low' dose, respectively.

The long-term metabolic effects of bedtime uncooked cornstarch ingestion, 0.55 g/kg body weight ('high dose'), were studied in 14 Type 2 diabetic patients. The design was a placebo controlled, double-blind, randomized cross-over study, with 7 weeks in each period and at least 11 weeks of washout. The patients were investigated three times: at baseline and after each of the treatment periods. Effects were expressed as Δcornstarch-Δplacebo.

The late nocturnal insulin concentrations were increased by 5.1±1.6 mU/l (p<0.01) between 02.00 and 07.00 h after the high dose of uncooked cornstarch. This was associated with a 32% suppression of the nocturnal plasma FFA level (p<0.01). The FFA concentration at 07.00 h also remained significantly suppressed after bedtime cornstarch ingestion (p<0.05). The 6-h incremental blood glucose level after breakfast was 36% lower (p<0.05) and the post-breakfast insulin secretory response, measured as Δ C-peptide, was enhanced by 40% at 120 minutes (p<0.05). However, there were no effects either on insulin sensitivity, on the nocturnal, fasting or postprandial lipid levels, or on the $HbA_{1c}$ levels by cornstarch ingestion. Patients characterized by low initial $HbA_{1c}$ and fasting blood glucose level were identified as "responders", ie, these patients improved their $HbA_{1c}$ levels ($\Delta HbA_{1c}$ 0.4±0.1%). Conversely, patients with high initial blood glucose levels and low nocturnal insulin secretion had an adverse effect of the cornstarch regimen on the $HbA_{1c}$ levels ($\Delta HbA_{1c}$ 0.5±0.2%).

The long-term effects of a 'low' close of uncooked cornstarch, 0.30 g/kg body weight, were studied in 24 patients with mild Type 2 diabetes. Each patient was pair-wise matched with another patient for BMI, fasting blood glucose and $HbA_{1c}$ level. Each pair was randomly stratified to cornstarch and placebo treatment in a double-blind, parallel fashion. Effects were measured as chances from baseline in morning fasting blood glucose and $HbA_{1c}$ level after 4 and 7 weeks of treatment.

The low dose of uncooked cornstarch was associated with significantly improved fasting blood glucose concentrations compared to the starch-free placebo after both 4 and 7 weeks by, on average, 0.8±0.4 (p<0.05) and 0.9±0.4 mmol/l (p<0.05), respectively. However, the $HbA_{1c}$ levels were similar.

In Table 2 below there is shown a multiple regression analysis of relationships between metabolic variables and $HbA_{1c}$. The data in this table show that improved glycemic control by bedtime carbohydrate supplement (BCS) is dependent on a preserved endogenous insulin secretion. Bedtime carbohydrate ingestion in people with impaired glucose tolerance may alleviate the "lypotoxic" effect of FFA on pancreas, as well as their effects on systemic glucose production.

TABLE 2

Multiple regression analysis of relationships between metabolic variables and $HbA_{1c}$.

| Dependent variable | Independent variables | p-value | Stand. Coeff. | Model r-value |
|---|---|---|---|---|
| $HbA_{1c}$ | Nocturnal insulin AUC | 0.005 | −0.579 | 0.87 |
|  | Fasting blood glucose | 0.042 | 0.439 |  |
|  | Nocturnal FFA AUC | 0.100 | 0.339 |  |

AUC, area under curve; FFA, free fatty acids.

EXAMPLE IV

Type 2 diabetic patients were recruited by means of advertisement in a local newspaper. Four of the patients had previously participated in Example III. Eight patients controlled their diabetes with sulfonylurea agents (glipizide or glibenclamide) and, in two patients, this was combined with metformin. Two patients were treated with metformin and six with diet alone. Their mean body weight was similar to that of the patients in Example II. Six patients had a BMI <27 kg/m$^2$. All except one had a waist-hip ratio>0.85 (women) and >0.90 (men).

The effects of bedtime ingestion of 0.55 g of uncooked cornstarch/kg body weight were studied in Type 2 diabetic patients.

The overnight second-meal effect of bedtime supplements containing "rapid" or "slow" starch was examined in a randomized, cross-over study with three test-periods. Each test-period consisted of two days on a standardized diet, followed by a breakfast tolerance test on the third morning. Sixteen patients with Type 2 diabetes participated. Two different bedtime (22.00 h) CHO supplements (0.46 g available CHO/(kg body weight) were compared to a starch-free placebo ('normal' food regimen). The CHO's were provided as uncooked cornstarch (slow-release CHO) or white bread (rapid CHO).

In the mornings after the different bedtime meals we found similar fasting glucose, insulin, FFA and lactate levels. However, the IAUC for glucose after breakfast was 21% less following cornstarch compared to placebo consumption the previous evening (406±46 vs. 511±61 mmol*min*$1^{-1}$, p<0.01). In contrast, the post-breakfast glucose IAUC after white bread was 451±57 mmol*min*1$^-$1, which did not differ significantly from the levels during the placebo period.

An in vitro starch digestibility analysis was undertaken for white bread, uncooked cornstarch and pumpernickel-bread with 100% whole kernels. Uncooked cornstarch contained ~4 times as much slowly digestible starch as compared to white bread and half the amount of rapidly digestible starch. Uncooked cornstarch and pumpernickel bread contained similar amounts of slowly and rapidly digestible starch (Table 2).

TABLE 3

Starch digestibility in vitro

| | Types of starch[1] | | | | Total starch (TS) |
|---|---|---|---|---|---|
| | Rapidly digestible starch | | Slowly digestible starch | | |
| | g/100 g | (% of TS) | g/100 g | (% of TS) | g/100 g |
| Uncooked cornstarch, dry | 34.3 | (38%) | 49.2 | (55%) | 89.1 |
| Uncooked cornstarch, wet for 48 h | 31.3 | (35%) | 51.5 | (57%) | 89.7 |
| White bread | 42.1 | (88%) | 5.8 | (12%) | 47.9 |
| Pumpernickel bread | 15.6 | (48%) | 16.5 | (51%) | 32.2 |

[1]Resistant starch not shown

Since various changes in the embodiments set forth above are obvious to the skilled artisan it is to be understood that the specific features and embodiments described above are to be interpreted as illustrative and not limiting ones,

What is claimed is:

1. A method for improving glucose tolerance in a human suffering from impaired glucose tolerance including both IGT and Diabetes Mellitus Type 2, comprising ingesting a therapeutic amount of slow-release starch at bedtime.

2. A method according to claim 1 for improving postprandial glucose tolerance.

3. A method according to claim 1 supplemented by further administration of slow-release carbohydrate before at least one of the following day's meals.

4. A method according to claim 1, wherein said slow-release carbohydrate is cornstarch, preferably contained in a palatable carrier.

5. A method according to claim 4, wherein said carrier is a liquid or gel.

6. A method according to claim 4, wherein said carrier is a carbohydrate other than starch.

7. A method according to claim 5, wherein said carrier is supplemented with a non-glucose sweetener.

8. A method according to claim 7, wherein said sweetener is selected from fructose, sorbitol, maltitol and artificial sweeteners.

9. A method according to claim 8, wherein said artificial sweeteners are selected from saccharine, aspartame and acesulfame.

10. A method according to claim 1, wherein the amount of slow-release carbohydrate ingested is from about 0.1 to about 1.

11. A method according to claim 2 supplemented by further administration of slow-release carbohydrate before at least one of the following day's meal.

12. A method according to claim 2, wherein said slow-release carbohydrate is cornstarch, preferably contained in a palatable carrier.

13. A method according to claim 3, wherein said slow-release carbohydrate is cornstarch, preferably contained in a palatable carrier.

14. A method according to claim 11, wherein said slow-release carbohydrate is cornstarch, preferably contained in a palatable carrier.

15. A method according to claim 6, wherein said carrier is supplemented with a non-glucose sweetener.

16. A method according to claim 2, wherein the amount of slow-release carbohydrate ingested is from about 0.1 to about 1 g per kg body weight.

17. A method according to claim 2, wherein the amount of slow-release carbohydrate ingested is from about 0.2 to about 0.7 g per kg body weight.

18. A method according to claim 3, wherein the amount of slow-release carbohydrate ingested is from about 0.1 to about 1 g per kg body weight.

19. A method according to claim 4, wherein the amount of slow-release carbohydrate ingested is from about 0.1 to about 1 g per kg body weight.

20. A method according to claim 1, wherein the amount of slow-release carbohydrate ingested is from about 0.2 to about 0.7 g per kg body weight.

* * * * *

UNITED STATES PATENT AND TRADEMARK OFFICE
CERTIFICATE OF CORRECTION

PATENT NO. : 6,316,427 B1
DATED : November 13, 2001
INVENTOR(S) : Mette Axelsen et al.

It is certified that error appears in the above-identified patent and that said Letters Patent is hereby corrected as shown below:

<u>Title page,</u>
Please add the following Assignee:

-- [73] Assignee: METCON MEDICIN AB
Lidingö, Sweden --

Signed and Sealed this

Fourth Day of June, 2002

*Attest:*

JAMES E. ROGAN
*Attesting Officer*    *Director of the United States Patent and Trademark Office*